United States Patent [19]
Holmstrand et al.

[11] Patent Number: 5,978,548
[45] Date of Patent: Nov. 2, 1999

[54] DEVICE FOR GASIFYING LIQUID AND FOR METERING THE GAS THEREBY OBTAINED

[75] Inventors: Niklas Holmstrand, Brottby; Rune Nyman, Solna, both of Sweden

[73] Assignee: Datex Engstrom AB, Sweden

[21] Appl. No.: 09/051,190

[22] PCT Filed: Sep. 26, 1996

[86] PCT No.: PCT/SE96/01205

§ 371 Date: Apr. 2, 1998

§ 102(e) Date: Apr. 2, 1998

[87] PCT Pub. No.: WO97/12642

PCT Pub. Date: Apr. 10, 1997

[30] Foreign Application Priority Data

Oct. 2, 1995 [SE] Sweden .................................. 9503399

[51] Int. Cl.⁶ .......................... F22B 29/06; A61M 15/00; A61M 16/00
[52] U.S. Cl. ............... 392/397; 128/203.12; 128/203.26; 128/203.27
[58] Field of Search ..................... 392/394, 396, 392/397, 398, 400, 401, 402; 128/203.12, 203.13, 203.14, 203.16, 203.17, 203.26, 203.27

[56] References Cited

U.S. PATENT DOCUMENTS

| | | |
|---|---|---|
| 2,507,464 | 5/1950 | DeAndrande So ..................... 431/208 |
| 2,785,271 | 3/1957 | Baly ........................................ 392/400 |
| 4,276,243 | 6/1981 | Partus ..................................... 392/402 |
| 4,682,010 | 7/1987 | Drapeau et al. .................... 128/203.27 |
| 4,693,853 | 9/1987 | Falb et al. . |
| 5,146,915 | 9/1992 | Montgomery ...................... 128/203.14 |
| 5,197,462 | 3/1993 | Falb et al. .......................... 128/203.14 |
| 5,243,973 | 9/1993 | Falb et al. . |
| 5,390,665 | 2/1995 | Leach ................................. 128/203.12 |

FOREIGN PATENT DOCUMENTS 231 513   8/1987   European Pat. Off. .

*Primary Examiner*—Teresa Walberg
*Assistant Examiner*—Sam Paik
*Attorney, Agent, or Firm*—Pillsbury Madison & Sutro LLP

[57] ABSTRACT

Device for gasifying liquid anaesthetic, for example, and for metering the gas thereby obtained to a stream of fresh gas. The device includes a pressurized source of the liquid which is to be gasified, a gasification chamber, heating members, and a fluid-conducting member. The gasification chamber is accommodated in an elongate gasification housing whose lower part has an inlet for liquid from the source. The member for supplying the gas in a metered manner to the stream of fresh gas comprises a metering housing connected to an upper part of the gasification housing and having a metering valve. The heating members are arranged on the outside of an intermediate part of the gasification housing, in order to form a warm housing section. This housing section communicates at the bottom with the inlet, and does so via a lower heat-insulating housing section, and it is connected at the top to the upper part.

8 Claims, 2 Drawing Sheets

DEVICE FOR GASIFYING LIQUID AND FOR METERING THE GAS THEREBY OBTAINED

This application is the national phase of international application PCT/SE96/01205 filed Sep. 26, 1996 which designated the U.S.

The present invention relates to a device of the general type specified in the first part of claim 1.

Such a device is intended for gasifying liquid, especially liquid anaesthetic, and for metering the gas thereby obtained to a stream of fresh gas, especially in an anaesthesia apparatus.

STATE OF THE ART

For a gasification chamber of the abovementioned type, the general or principle is that the chamber constitutes a cavity or closed space where the liquid in question, which is accordingly a liquid anaesthetic when metering gas to a fresh gas stream in an anaesthesia apparatus, is gasified and is then conveyed onwards to, and metered into, the stream of fresh gas. The basic principle of gasification is that the liquid in question is vaporized by being made to boil, as a result of which a 100% saturated vapour is obtained. Since the liquid which is made to boil (vaporized) and the vapour are under pressure, it can be metered in gaseous form into the stream of fresh gas by means of opening a valve in the line via which the metering gas is introduced into the stream of fresh gas. It is important in this respect that the vapour (gas) thus generated is cooled only after it has been metered into the stream of fresh gas. Otherwise, it would be condensed, i.e. liquid would then be metered into the stream of fresh gas as would the vapour, and this would lead to the vapour pressure in the fresh gas becoming unpredictable and too high.

For an example of a known device of the type mentioned in the introduction, reference may be made to the metering and gasifying device which is described in European Patent Specification 0 231 513. This known device is intended especially for supplying anaesthetic gas to a stream of fresh gas in an anaesthesia apparatus. This device comprises a source of gas at constant pressure, a second source containing a liquid which is to be gasified, a gasification chamber and a metering line through which the gas is conveyed from the chamber to a mixing point where it is mixed with another gas (which is the fresh gas where the application involves an anaesthetic gas apparatus), and a valve device which is arranged to deliver a defined dose of gas for each metering stroke of a control valve in the valve device. The distinguishing feature of this known metering and gasifying device is that the gasification chamber is intended to be kept at a constant pressure and, by means of a controllable heating device, to be maintained at a temperature which is such that the liquid fed from the liquid source into the gasification chamber is in the main gasified directly, so that when equilibrium has been reached, no more liquid is supplied from the liquid source to the gasification chamber than is dosed/metered by means of the valve device in the metering line.

Another example of a known metering device intended for the same medical engineering application is found in U.S. Pat. No. 5,243,973.

OBJECTS OF THE INVENTION

The primary object of the present invention is to make available a device in which the free liquid surface inside the gasification chamber—which is located somewhere between the lower part of the chamber (containing the liquid phase) and the upper part of the chamber (containing the gas phase)—can be maintained at a virtually constant level in the gasification chamber.

The underlying idea of the solution which is provided by the invention to this problem will be that the gasification chamber is designed in such a way that a well-defined heating zone, which can be controlled/monitored by simple means, is obtained in an intermediate area in the gasification housing in which the gasifi-cation chamber is accommodated.

A secondary object of the invention will be that the gasification housing can be designed in a way which is simple and reliable in terms of construction and so that any variations in the level of the liquid surface inside the gasification chamber can be easily detected, which is made easier by the fact that the gasification housing (and with it the gasification chamber) can have a relatively elongate construction so that the gasification chamber will have a transverse dimension which is substantially smaller than the axial longitudinal dimension of the chamber.

DISCLOSURE OF THE INVENTION

According to the invention, the abovementioned objects are achieved by virtue of the fact that the device specified in the introduction has the features specified in the characterizing clause of Patent claim 1.

Features which represent further developments of the invention, and which contribute to what is from various standpoints an optimum solution to the problem, are also to be found in dependent claims 2–8.

According to the invention, a constructional embodiment is chosen in which the gasification chamber is accommodated in an elongate gasification housing, which has a lower part provided with an inlet for liquid from the source, and the member for supplying the gas in a metered manner to the stream of fresh gas comprises a metering housing connected to an upper part of the gasification housing and having at least one metering valve. The heating members are in this case arranged on the outside of an intermediate part of the gasification housing, situated in the area between the upper part and the lower part of the gasification housing, in order to form a warm housing section which establishes the abovementioned well-defined temperature zone. This warm housing section communicates at the bottom with the lower part of the gasification housing, provided with the inlet, via a lower heat-insulating housing section, and is connected at the top to the upper part of the gasification housing via a corresponding upper heat-insulating housing section.

The gasification housing is preferably designed in such a way that the boundary wall of the gasification chamber is formed by a cylindrical jacket surface. This is achieved, for example, by the gasification housing being a tubular housing which is expediently arranged essentially vertically or at least at a relatively acute angle in relation to the vertical.

In order to make it easier to maintain a well-defined heating zone in the warm housing section, it is expedient that the gasification housing be made of a material with good heat conductivity, for example brass, in which case the intermediate part of the housing preferably has a greater wall thickness than the two heat-insulating housing sections which are connected to the ends of the intermediate part. The transition between the intermediate part of greater wall thickness of the gasification housing and each adjoining heat-insulating housing section of lesser wall thickness generates a marked temperature gradient in the wall material, and the lesser wall thickness of the heat-insulating housing sections means that heat conduction away from the warm housing section formed by the intermediate part is minimized in the heat-insulating housing sections.

The lower part of the gasification housing provided with the inlet (with the inlet for the liquid from the source) is preferably designed as a cold housing section which is arranged in heat-conducting communication with a separate cooling base. This cooling base serves to maintain the liquid surface inside the gasification chamber at an acceptable level in the event of the internal temperature in the chamber for some reason tending to become too high.

To keep the temperature conditions as constant as possible within the intermediate part of the gasification housing, which constitutes the warm housing section, the intermediate part is expediently provided with an effective heat insulation surrounding at least that area of the intermediate part which is provided on the outside with the heating members, which expediently consist of one or more electrical heating elements. These heating elements, which can consist of heat foils, are in this case arranged on the outside of the wall of the inter-mediate part of the housing and surround this wall at least over a fairly large part of its longitudinal extent.

For monitoring the temperature conditions in the warm housing section, a suitable type of temperature sensor, for example a thermistor, is arranged preferably in the area of the lower end of the intermediate part of the housing, on the inside of the housing wall. The output signal from this temperature sensor can then be used for controlling the power of the electrical heating members. Similarly, a temperature sensor may expediently be arranged on the inside of the housing wall in the area of the upper end of the intermediate part of the housing. The output signal from this temperature sensor can be used in an alarm function for temporarily interrupting the supply of gas to the stream of fresh gas or for interrupting the gasification of liquid in the gasification chamber by interrupting the current supply to the electrical heating members which surround the intermediate part of the gasification housing.

The metering housing mounted on the upper part of the gasification housing preferably comprises a valve plate provided with a separate electrical heating element, and, connected to this valve plate, a housing part which conveys the fresh gas and which has a continuous passage for the fresh gas. One end off this gas passage constitutes the inlet for the stream of fresh gas, while the other end of the passage constitutes the outlet for the fresh gas which, via a channel adjoining the gas passage inside the housing part, has been enriched with gas generated in the gasification chamber. For effecting this supply of gas to the stream of fresh gas, the gas passage through the housing part is in communication with the gasification chamber via channels in the metering valve, the valve plate, and the housing part connected thereto.

The valve plate, which can be designed, for example, as a rectilinear plate or an otherwise designed construction, not only bears the metering valve, which can be a solenoid valve for example, but also a backflow valve. The purpose of this backflow valve is to use separate backflow gas, for example oxygen or air, to force non-gasified liquid back from the gasification chamber to the liquid source after the gasification in the gasification chamber has ended. Such a backflow is needed, for example, when replacing the liquid which is to be gasified in the gasification chamber. The backflow valve then communicates, on the one hand, with a backflow gas source via a channel in the valve plate, and, on the other hand, communicates with the gasification chamber via channels in the valve plate.

The metering valve is expediently arranged axially in line with the gasification housing on the side of the valve plate directed away from the housing, while the backflow valve is expediently arranged on the same side of the valve plate as the gasification housing. With the gasification housing arranged vertically, the metering valve is then directed straight up from the top side of the valve plate, while the backflow valve is directed straight down from the underside of the valve plate, parallel to the preferable tubular gasification housing.

BRIEF DESCRIPTION OF THE FIGURES IN THE DRAWING

The invention will now be described and explained in greater detail below, with reference to the attached drawings which show an embodiment of the device according to the invention. In the drawings.

Figure 5:
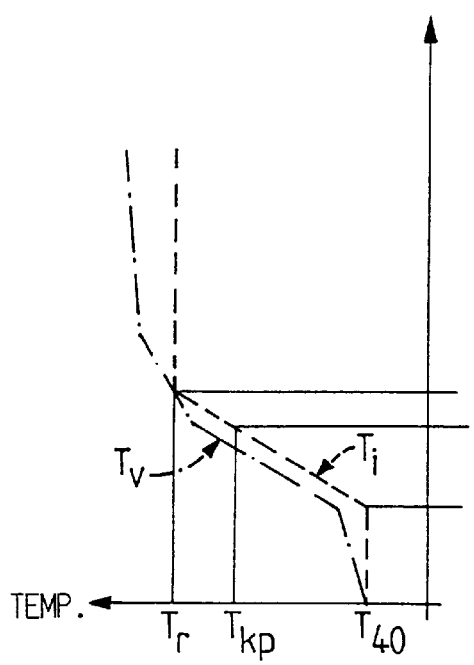
Figure 4:
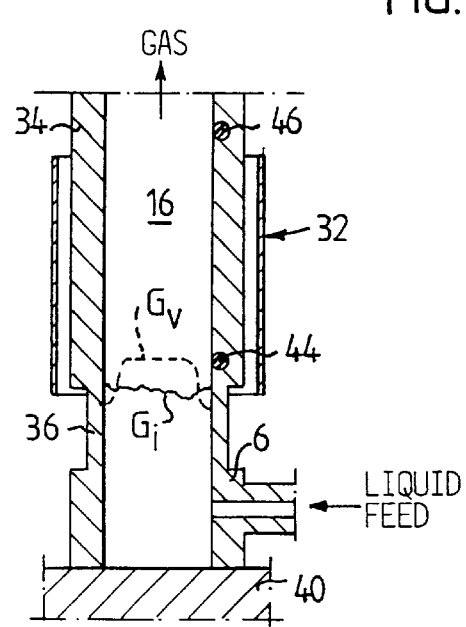
FIG. 4 shows a longitudinal section through the lower half of the gasification housing of a device according to the invention, shown in a very schematic representation as background to the temperature curves in FIG. 5.

FIG. 5, finally, shows the ideal temperature profile and a more realistic temperature profile for the fluid (the liquid/gas (vapour)) inside the part, shown in FIG. 4, of the gasification chamber in the gasification housing of the device.

DESCRIPTION OF ILLUSTRATIVE EMBODIMENTS

Figure 1:
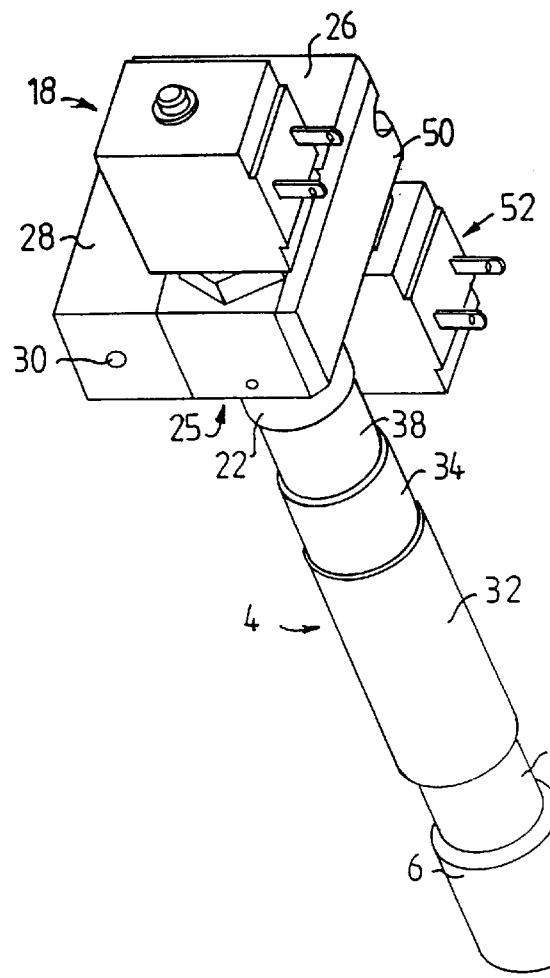
FIG. 1 shows major parts and members of a device according to the invention, seen in perspective.

FIG. 1 shows a perspective representation of major parts and members of a device according to the invention intended for gasifying liquid. In this particular case, the device is intended for gasifying liquid anaesthetic, and for metering the anaesthetic gas thereby obtained to a stream of fresh gas for an anaesthesia apparatus (not shown). Connected to the device in this case is a liquid source 2, not shown in FIG. 1, but indicated in FIG. 2, which liquid source is under preferably constant pressure and contains the liquid anaesthetic which is to be gasified in the device.

Figure 2:
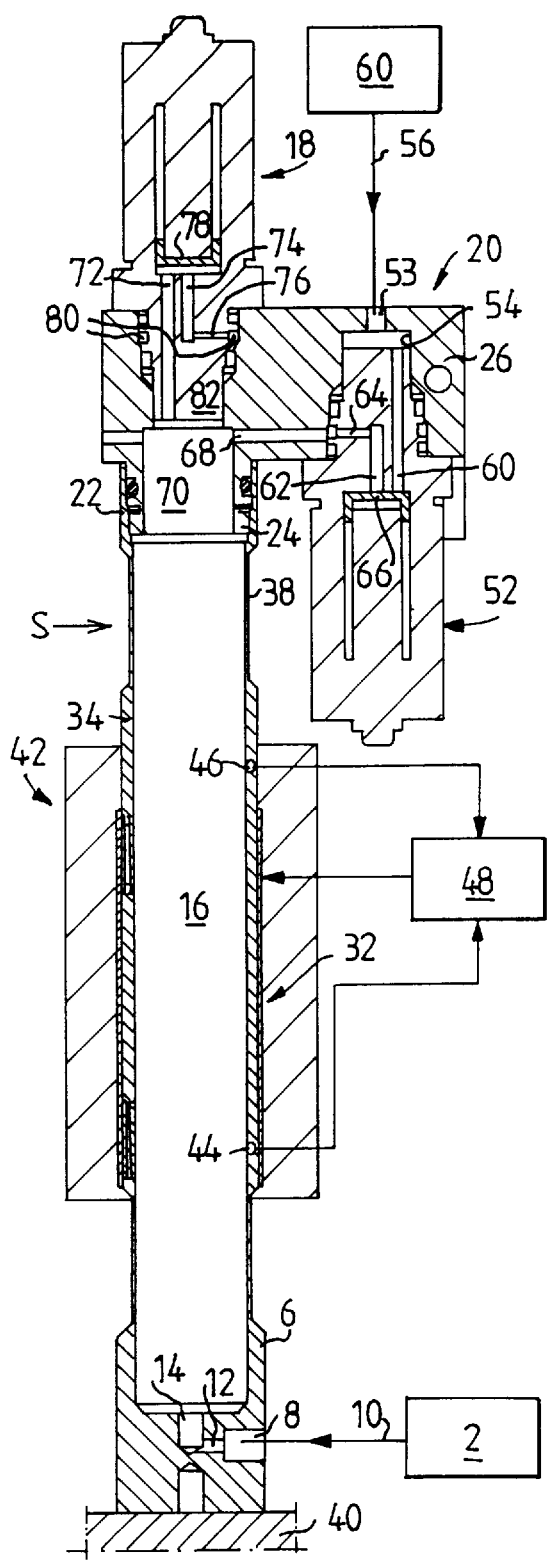
FIG. 2 shows a longitudinal section through the device shown in FIG. 1 and FIG. 3, along the line of sectioning II—II in FIG. 3.
Figure 3:
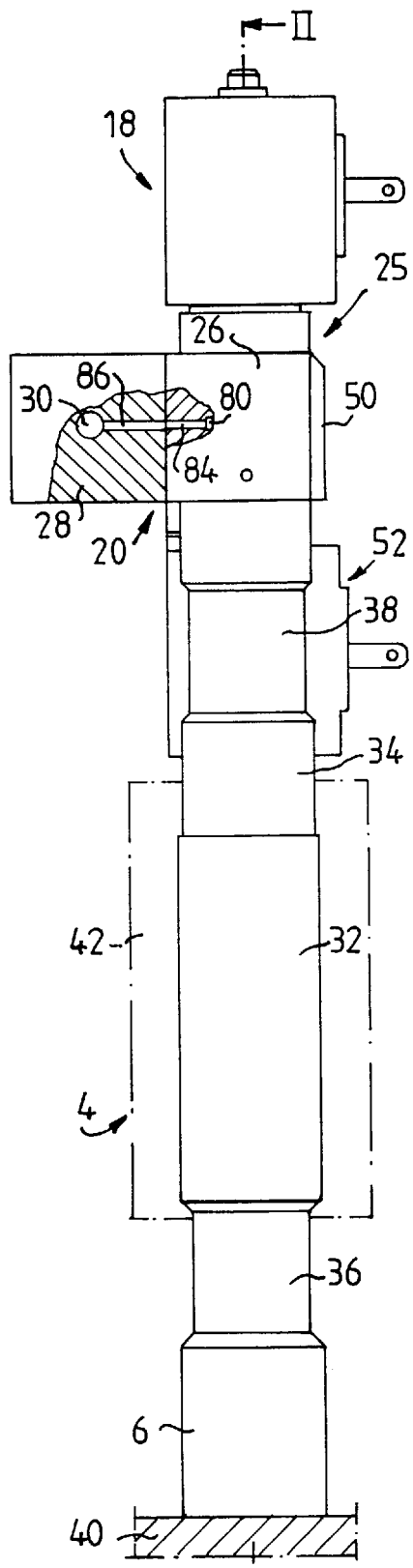
FIG. 3 shows a side view of the device in accordance with FIG. 2, as seen in the direction indicated by the arrow S in FIG. 2.

The device shown in FIGS. 1–3 comprises a tubular gasification housing 4 with a lower part 6 provided with an inlet 8 for the liquid anaesthetic supplied from the source 2 through a line 10. This liquid anaesthetic flows in from the inlet 8 via a pair of channels 12 and 14 at the lower end of a cylindrical gasification chamber 16 accommodated in the gasification housing 4. At the upper end of the gasification chamber 16 there is a fluid-conducting member 20 which is provided with a metering valve 18 and is used for supplying gas in a metered manner from the chamber 16 to the stream of fresh gas for the abovementioned anaesthesia apparatus (not shown here). The gasification housing 4 has an upper end part 22 which is connected tightly to a downwardly directed tube section 24 on the underside of the fluid-conducting member 20.

As can be seen from FIGS. 2 and 3, the member 20 comprises a metering housing 25 which is connected to the upper part 22 of the gasification housing and which in turn comprises a parallelepipedal valve plate 26 and, connected to the latter, a housing part 28 which conveys fresh gas and has a continuous gas passage 30 for the stream of fresh gas which is added, inside the housing part 28, to the gas from the gasification chamber 16. The housing part 28 can constitute an integrated part of the valve plate 26. The flow path of the gas from the gasification chamber 16 to the passage 30 for fresh gas will be described hereinbelow.

As can be seen from FIGS. 1–3, the gasification housing 4 is provided on the outside with heating members 32. These heating members expediently consist of one or more electrical heating elements, preferably of the heat foil type.

As can be seen in particular from FIG. 2, the heating members 32 are arranged on the outside of an intermediate part 34 of the gasification housing which is located between the upper part 22 of the gasification housing 4 and the lower part 6, and which has a comparatively thick wall. This intermediate part 34, which constitutes the warm housing section of the device, communicates at the bottom with the lower part 6 of the gasification housing, provided with an inlet, and does so via a lower heat-insulating housing section 36 which has a comparatively thin wall. Similarly, the intermediate part 34 communicates at the top with the upper part 22 of the gasification housing 4 via an upper heat-insulating housing section 38 which has a comparatively thin wall.

The gasification housing 4, which is a tubular housing in the embodiment shown, is made of a material with good heat conductivity, such as brass, for example. As can be seen from FIG. 2, the intermediate part 34 of the classification housing 4, and also the upper part 22 and lower part 6 of the housing, have a considerably greater wall thickness than the two heat-insulating housing sections 36 and 38. These two thin-walled, heat-insulating housing sections in this way function as temperature insulators in the axial direction of the gasification housing. The lower part 6 of the gasification housing, provided with the inlet, forms the cold housing section of the device, which cold section is expediently in direct heat-conducting communication with a cooling base 40 which is only schematically indicated and whose temperature is designated $T_{40}$ in FIG. 5.

The heating members 32 surrounding the intermediate part 34 of the gasification housing surround the said intermediate part of the housing over at least a fairly large part of its longitudinal extent. In order to maintain the desired temperature conditions and temperature gradients in that part of the gasification chamber 16 located in the intermediate part 34, an outer, sleeve-like heat insulator 42 is arranged around the gasification housing 4, at least over that part of the housing where the heating members 32 are present.

In the area of the lower end of the intermediate part 34 of the housing, a temperature sensor 44, for example a thermistor, is arranged on the inner side of the housing wall, the output signal from this temperature sensor 44 serving to control the power of the electrical heating members 32. In the area of the upper end of the intermediate part 34 of the housing, and again on the inner side of the housing wall, there is a further temperature sensor 46 whose output signal is used in an alarm function, for example for temporarily interrupting the metered supply of gas to the stream of fresh gas or for interrupting the gasification of liquid in the gasification chamber 16. FIG. 2 shows diagrammatically a control means 48 acted on by the temperature sensors 44 and 46 and used for controlling the current supply to the heating members 32.

We now pass to a more detailed examination of the fluid-conducting member 20 located at the upper end of the gasification housing 4, with reference being made in particular to FIG. 2 and FIG. 3.

The fluid-conducting member 20, which thus manages the supply of gas from the chamber 16 to the stream of fresh gas in the passage 30, consists of a metering housing which comprises the valve slate 26 provided with a separate electrical heating element 50, and the housing part 28 connected to the rear side of the valve plate and having the continuous gas passage 30. The fresh gas flowing to the anaesthesia apparatus (not shown here) enters the gas passage 30 at the inlet end thereof and then, after having been enriched with metered fresh gas inside the housing part 28, flows out from the passage 30 via the outlet end thereof.

In addition to the metering valve 18, which can be a solenoid valve for example, the valve plate 26 also has a backflow valve 52. This backflow valve serves, with the aid of backflow gas, for example oxygen or air, to force residual non-gasified liquid back from the gasification chamber 16 to the liquid source 2 after gasification in the gasification chamber has ended. This situation arises, for example, when replacing the liquid which is to be gasified in the gasification chamber 16. The backflow valve 52, which is mounted in a bore 54 in the valve plate 26, communicates at the top with a backflow gas source 60 via a line 56 and an inlet 58. Inside the backflow valve 52 there are a pair of axial channels 60 and 62 and a radial channel 64 adjoining the upper end of the channel 62. When the movable valve element 66 of the valve is situated in a lower position, gas can flow from the inlet 58 via the channels 60, 62 and 64 to the horizontal channel 68 in the valve plate 26. The channel 68 opens into a bore 70 in the valve plate 26, which bore 70 is in direct and open communication with the upper end of the gasification chamber 16. When the gasified anaesthetic is to be metered into the fresh gas which is flowing through the passage 30, the backflow valve 52 is of course closed, i.e. the valve element 66 is then situated in an upper closure position which prevents mutual communication between the channels 60 and 62 in the backflow valve 52.

The metering valve 18, for its part, contains the two axial channels 72 and 74 and also the transverse channel 76 issuing radially from the lower end of the channel 74. The channels 72 and 74 communicate with each other when the movable valve element 78 of the metering valve 18 is situated in a raised opening position. By contrast, when the valve element 78 has been switched by magnetic actuation to a lower closure position, fluid cannot flow between the channels 72 and 74. The radial channel 76 opens out into a circular track 80 on the outside of the attachment part 82 of the metering valve 18 held in the valve plate 26. As can be seen from FIG. 3, the circular track 80 communicates with the fresh gas passage 30 via a radial channel 84 in the valve plate 26 and a channel 86 in the housing part 28 coaxially adjoining the channel 84. The channel 86 opens into the fresh gas passage 30 and the supply of gas from the gasification chamber 16 to the fresh gas in the passage 30 thus takes place at the point where the channel 86 opens into the passage 30.

During ongoing gasification in the gasification chamber 16, the backflow valve 52 is closed, and the gas from the chamber 16 can then flow from the bore 70 via the channels 72, 74 and 76 and the circular track 80 and the coaxial channels 84 and 86 to the fresh gas passage 30 where the mixing takes place.

The control of the gasification in the chamber 16 will now be described in brief with reference to the diagrammatic FIGS. 4 and 5 which describe the function and in which those parts directly corresponding to the embodiment according to FIGS. 1–3 have been given the same designations as in these three figures.

The lower part of the gasification chamber 16 will at all times contain the liquid phase of the supplied liquid anaesthetic, while the upper part of the gasification chamber 16 will contain the gas phase of the anaesthetic. Somewhere between these there will be a liquid surface G. In compliance with the primary objective of the invention, the level of this surface will be maintained as constant as possible. To achieve this, the temperature of the walls of the gasification chamber must be controlled and monitored carefully. The lowermost part of the gasification chamber will be maintained at a temperature which lies below the boiling point of the anaesthetic, and that part of the gasification chamber situated above the lowermost part will be maintained at a temperature in excess of the boiling point. Between these two temperature zones there is a gasification housing section 36 with comparatively thin walls, which section functions as a temperature insulator. The temperature profile there is not known in detail, but it has to be a continuous function of the height and must increase constantly. The thick walls of the upper housing sections have a high heat conductivity (brass is a good conductor of heat) which keeps the temperature virtually constant in the vertical direction. The ideal temperature profile is designated $T_i$ and is shown by a dashed line in FIG. 5. At the lower end of the warm housing section (to the inside of the heating members 32) there is a temperature sensor 44 which is used for temperature control, i.e. this is the location which the control means attempts to maintain at the set temperature $T_r$ for the warm section. At the upper end of the warm housing section there is a temperature sensor 46 whose detected temperature will at all times lie above the boiling point. Should this temperature drop below the boiling point ($T_{kp}$), then the level of the liquid surface is probably too high up in the gasification housing 4. If this happens immediately after a large, gradual increase in the metering, then it should be possible to stop the metering for a short time in order to give the heating members 32 the possibility of "catching up". If, on the other hand, this happens during normal metering, then it is a matter of a serious error, and an alarm signal must then be generated and the gasification interrupted.

In practice, the temperature profile will not of course be as favourable as in the ideal case which is represented in FIG. 5 by the dashed line $T_i$. In practice, the temperature will not be constant in the vertical direction in the sections without heat insulating. In the horizontal direction, the anaesthetic will not have the same temperature as the walls. A somewhat more realistic temperature profile is shown by the dot-and-dash line in FIG. 5 and is designated $T_v$. The phase boundary between the liquid phase and gas phase of the anaesthetic is designated $G_i$ in FIG. 4 for the ideal case and $G_v$ for the more realistic "actual" case.

We claim:

1. Device adapted to gasify a liquid and arranged for metering the gas thereby obtained to a stream of fresh gas, the device comprising a source (2) of a liquid which is to be gasified, a gasification chamber (16) communicating with the liquid source and having heating members (32), and a fluid-conducting member (20) provided with a metering valve (18) and adapted to supply gas in a metered manner from the chamber (16) to the stream of fresh gas, characterized in that the gasification chamber (16) is accommodated in an elongate gasification housing (4), having a lower part (6) provided with a liquid inlet (8) for supplying liquid from the source, fluid-conducting member (20) comprises a metering housing connected to an upper part (22) of the gasification housing (4) and having at least one metering valve (18), that the heating members (32) are arranged on the outside of an intermediate part (34) of the gasification housing, situated between the upper and lower parts (22 and 5) of the gasification housing (4), in order to define a warm housing section, that the warm housing section,which is provided with said heating members (32), communicates at the bottom with the lower housing part (6) with the inlet (8), and does so via a lower heat-insulating housing section (36), that the warm section is connected at the top to the upper housing part (22) via an upper heat-insulating housing section (38),and that temperature sensors (44,46) are arranged in the intermediate housing part (34) and connected to act on a control means (48) controlling the power supply to the heating members (32).

2. Device according to claim 1, characterized in that the gasification housing is a tubular housing (4) made of a material with, good heat conductivity, for example brass, and the intermidiate part (34) of the housing, and its upper and lower parts (22 and 6, respectively), have a greater wall thickness than the two heat-insulating housing sections (36, 38), and in that the lower part (6) of the gasification housing provided with the inlet forms a cold housing section which is arranged in heat-conducting communication with a cooling base (40).

3. Device according to claim 1, characterized in that the heating members consist of at least one electrical heating element (32), such as a heating foil, which is arranged on the outside of the wall of the intermediate part (34) of the housing and surrounds this wall at least over a fairly large part of its longitudinal extent.

4. Device according to claim 3, characterized in that a temperature sensor (44) is arranged in the area of the lower end of the intermediate part (34) of the housing, on the inside of the housing wall, the output signal from this temperature sensor (44) serving to control the power of the electrical heating members (32), and in that a temperature sensor (46) is arranged on the inside of the housing wall in the area of the upper end of the intermediate part of the housing, the output signal from this temperature sensor (46) being used in an alarm function for temporarily interrupting the supply of gas to the stream of fresh gas or for interrupting the gasification of liquid in the gasification chamber (16).

5. Device according to claim 1, characterized in that the metering housing, which is mounted on the upper part of the gasification housing, comprises a valve plate (26) provided with a separate electrical heating element (50), and, connected to this valve plate, a housing part (28) which conveys the fresh gas and which has a continuous gas passage (30) whose one end constitutes the inlet for the stream of fresh gas and whose other end constitutes the outlet for the fresh gas which has been enriched with metered gas, and which gas passage (30) communicates with the gasification chamber (16) via channels (70, 72, 74, 76, 80, 84, 86) in the metering valve (18), the valve plate (26), and the housing part (28) connected thereto.

6. Device according to claim 5, characterized in that the valve plate (26) not only bears the metering valve (18), which is preferably a solenoid valve, but also a backflow valve (52) which uses separate backflow gas, for example oxygen, to force non-gasified liquid back from the gasification chamber to the liquid source (2) after the gasification in the gasification chamber (16) has ended, for example when replacing the liquid which is to be gasified, and the backflow valve (52) communicates, on the one hand, with backflow gas source (60) via a channel (58) in the valve plate (26), and, or the other hand, communicates with the gasification chamber (16) via channels (68, 70) it the valve plate (26).

7. Device according to claim 6, characterized in that the metering valve (18) is arranged axially in line with the gasification housing (4) on the side of the valve plate (26) directed away from the housing, while the backflow valve (52) is arranged on the same side of the valve plate as the gasification housing.

8. Device according to claim 1, characterized in that the intermediate part (34) of the gasification hosing (4) is provided with a heat insulation means (42) surrounding at least that portion of the intermediate part- which bears the heating members (32).

* * * * *